United States Patent [19]

Simpson

[11] 4,011,323
[45] Mar. 8, 1977

[54] BI-4-[1-(QUINAZOLINYL-4)PIPERIDYLS] AND BIS 4-[1-(QUINAZOLINYL-4)PIPERIDYL-]ALKANES

[75] Inventor: William R. J. Simpson, Mendham, N.J.

[73] Assignee: Sandoz, Inc., E. Hanover, N.J.

[22] Filed: June 18, 1975

[21] Appl. No.: 588,003

Related U.S. Application Data

[63] Continuation-in-part of Ser. No. 451,977, March 18, 1974, abandoned, which is a continuation-in-part of Ser. No. 291,652, Sept. 25, 1972, abandoned.

[52] U.S. Cl. .................. 424/251; 260/256.4 Q; 260/256.5 R; 260/293.63; 260/340.3
[51] Int. Cl.² ................................ C07D 401/14
[58] Field of Search ............ 260/256.4 Q, 256.5 R; 424/251

[56] References Cited

UNITED STATES PATENTS 3,931,179  1/1976  Simpson .............. 260/256.4 Q
3,971,783  7/1976  Barnish et al. ......... 260/256.4 Q

OTHER PUBLICATIONS

Tietz, "Clinical Chemistry," pp. 153, 807–808.
White et al., "Principals of Biochemistry," (1968) pp. 974–977.

Primary Examiner—Donald G. Daus
Assistant Examiner—David E. Wheeler
Attorney, Agent, or Firm—Gerald D. Sharkin; Richard E. Vila

[57] ABSTRACT

Disclosed are bi-4-[1-(quinazolinyl-4)piperidyls] and bis{4-[1-(quinazolinyl-4)piperidyl]alkanes}, e.g. 1,3-bis{4-[1-(6,7-dimethylquinazolinyl-4)piperidyl]propane}, having pharmacological activity in animals and useful for example, as anti-obesity and anti-diabetic agents. Said compounds may be prepared by reacting a 4-haloquinazoline with bi-4-piperidyl or a bis(piperidyl-4)alkane.

52 Claims, No Drawings

BI-4-[1-(QUINAZOLINYL-4)PIPERIDYLS] AND BIS 4-[1-(QUINAZOLINYL-4)PIPERIDYL]ALKANES

This application is a continuation-in-part of application Ser. No. 451,977, filed Mar. 18, 1974, now abandoned, which in turn is a continuation-in-part of now abandoned application Ser. No. 291,652, filed Sept. 25, 1972, now abandoned.

The invention relates to chemical compounds which are bi-4-[1-(quinazolinyl-4)piperidyls] and bis{4-[1-quinazolinyl-4)piperidyl]alkanes} having pharmacological activity in animals and to pharmaceutical methods and compositions utilizing the pharmacological properties of said compounds.

The compounds of the present invention may be represented structurally by the following formula (I):

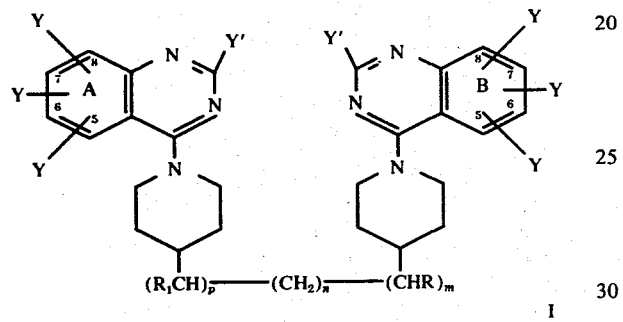

wherein
R and $R_1$ are independently hydrogen or alkyl of 1 to 4 carbon atoms,
$n$ is 0 to 4,
$m$ is 0 to 1,
$p$ is 0 or 1,
each Y is independently hydrogen, halo of atomic weight of from 18 to 80, i.e. fluoro, chloro and bromo, alkyl of 1 to 4 carbon atoms, alkoxy of 1 to 3 carbon atoms, alkylthio of 1 to 3 carbon atoms, hydroxy, formamido, trifluoromethyl, nitro, cyano, amino, hydroxylamino, N-monoalkylamino of 1 to 4 carbon atoms, N,N-dialkylamino in which each alkyl is of 1 to 3 carbon atoms, alkanoylamino of 2 to 4 carbon atoms, N-alkyl (of 1 to 3 carbon atoms), N-alkanoyl (of 2 to 4 carbon atoms) amino or N-alkyl (of 1 to 3 carbon atoms), N-formylamino or two adjacent Y together form 6,7-methylenedioxy or 6,7-ethylenedioxy (with the other Y on each A and B ring so substituted being hydrogen), subject to the proviso that: (1) adjacent Ys are not both tert-butyl; (2) no more than 2 Ys in each A and B ring are substituents selected from the group consisting of trifluoromethyl, nitro, cyano, hydroxy, formamido, alkylthio, amino, N-alkylamino, N,N-dialkylamino, hydroxylamino, alkanoylamino, N-alkyl, N-alkanoylamino and N-alkyl, N-formylamino; (3) when any Y in an A or B ring is amino, cyano, hydroxylamino, N-alkylamino, N,N-dialkylamino, alkanoylamino, formamido, N-alkyl, N-alkanoylamino or N-alkyl, N-formylamino, then any dissimilar Y is selected from the group consisting of hydrogen, halo, alkyl and alkoxy; and (4) when any Y is hydroxy, then no other Y is a dissimilar substituent selected from the group consisting of alkoxy and alkylthio, and
each Y' is independently hydrogen, halo of atomic weight of from 35 to 80 or alkyl of 1 to 4 carbon atoms, or a pharmaceutically acceptable acid addition salt thereof.

The invention also includes the 1-alkyl quaternary salts of certain compounds of the formula I, viz. the compounds of the formula Iq:

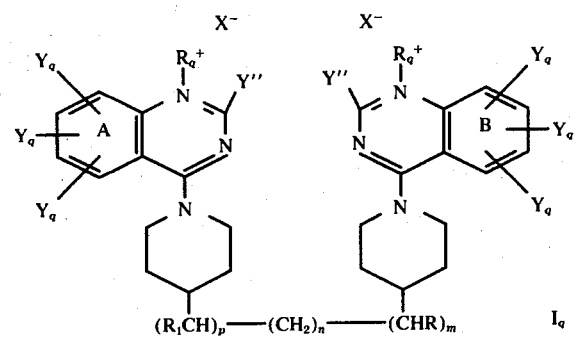

wherein
$m$, $n$ and $p$ are as defined above, and each
Yq is, independently, hydrogen, halo of atomic weight of from 18 to 80, alkyl of 1 to 4 carbon atoms, alkoxy of 1 to 3 carbon atoms, trifluoromethyl or nitro or two adjacent Yg together form 6,7-methylenedioxy or 6,7-ethylenedioxy (with the other Y on each A and B ring so substituted being hydrogen), subject to the provisos stated above, i.e. that: 1) adjacent Yq's are not both tert-butyl; and 2) no more than two Yq's in each A and B ring are substituents selected from the group consisting of trifluoromethyl and nitro,
$R_q$ is alkyl of 1 to 4 carbon atoms which is unbranched on the α-carbon atom,
X is a pharmaceutically acceptable inorganic anion, e.g. the iodide, bromide, chloride, hydroxide, sulfate and the like, and
Y" is hydrogen, halo of atomic weight of 35 to 80 or straight chain lower alkyl of 1 to 4 carbon atoms.

The compounds of the formula I may be prepared by reacting a compound of the formula II:

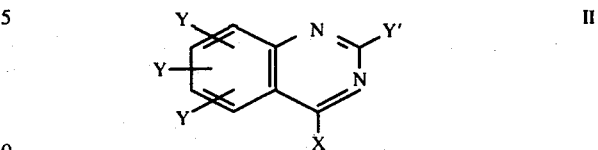

wherein
Y and Y' are as above defined and X is chloro, bromo or —WZ in which W is oxygen or sulfur and Z is alkyl of 1 to 4 carbon atoms, phenyl or benzyl, with a compound of the formula III:

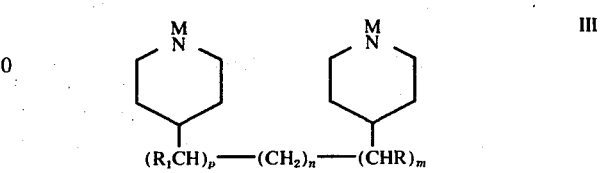

wherein
R, $R_1$, $m$, $p$ and $n$ are as defined, and M is hydrogen or an alkali metal, e.g. sodium.

The preparation of compounds of the formula I by reacting a compound of the formula II with a compound of the formula III is suitably carred out in an inert organic solvent at temperatures in the range of from 0° C. to 160° C., preferably 20° C. to 100° C. The reaction may, if desired, be conducted under an inert atmosphere, e.g., nitrogen, and is preferably carried out with a compound II in which X is halo, more preferably chloro, and with a compound III in which M is hydrogen. The mole ratio of the compound II to the compound III may vary fairly widely with very good results obtained at a ratio of 2:1 or somewhat higher. When employing a compound III in which M is hydrogen, the reaction is desirably carried out in the presence of an acid binding agent such as sodium carbonate or triethylamine. The inert organic solvents when M is hydrogen may be any of several of the well known conventional solvents such as the common aromatic solvents, e.g. benzene, the ethers such as dioxane and the lower alkanols such as isopropanol and the like, preferably a solvent which is useful under reflux conditions. When carrying out the reaction with a compound III in which M is an alkali metal, it is generally preferred to prepare such a compound III prior to combination with the compound II by reacting a compound III in which M is hydrogen in an inert organic solvent with a strong alkali metal base, i.e. a compound of known capability for converting a compound III in which M is hydrogen to a compound III in which M is an alkali metal, e.g. sodium hydride, butyl lithium and the like. The reaction is conveniently effected at from 0° C. to 50° C., preferably at about room temperature, in an inert solvent of conventional type which preferably can be conveniently employed as solvent for the preparation of the compound I. The more suitable such solvents are the lower boiling ethers, e.g. dioxane and tetrahydrofuran. The preparation of compounds I from the metallo substituted compound III is effected in an inert organic solvent, preferably an ether such as dioxane or tetrahydrofuran, at temperatures suitably from 0° C. to 100° C., preferably 10° C. to 50° C., and conveniently at about room temperature, and the reaction typically proceeds fairly quickly. The compounds I may also be prepared by reacting a compound II with a compound III in which M is hydrogen in an inert solvent such as an ether and in the presence of a strong alkali metal base (as above defined). Such reaction may also be effected at temperatures of from 0° C. to 100° C., preferably 10° C. to 50° C., and conveniently at room temperature. Two different compounds II in varying ratios to each other and to the compounds III may be employed to produce compounds I in which the 2 quinazoline moieties attached to the bis(piperidyl-4) moiety are different. Such mixed quinazoline compounds are suitably prepared, for example, by reacting a compound II with a compound III in about a 1:1 ratio followed by reacting the resulting product in a ratio of at least about 1:1 with a different compound II. The preferred compounds of the formula I are, however, those in which the two quinazolinyl moieties are the same. The reaction product of the formula I may be isolated from the reaction mixture resulting from the above-described preparation by working up by established procedures.

Certain of the compounds I of the invention may be employed to produce other compounds I of the invention by procedures which are generally well known and which in some instances may be preferred for the preparation of such compounds. For example, the compounds I in which one or more Y is nitro or amino may be employed in producing other compounds of formula I, particularly the compounds in which one or more Y is amino, cyano, hydroxy, hydroxylamino alkanoylamino, formamido, and N-monoalkylamino. Hence, the compounds I in which one or more Y is amino are preferably produced from a corresponding compound I in which one or more Y is nitro by subjecting the latter to reduction in a known manner. For example, the compounds I in which one or more Y is amino may be produced by subjecting a compound I in which one or more of the Y groups are nitro to the action of a suitable elemental metal reducing agent such as iron at elevated temperatures, e.g., 50° to 150° C., in an aqueous acidic medium, e.g., hydrochloric acid in an aqueous alcoholic solution. The compounds I in which one or more Y is amino may be also produced by subjecting a compound I in which one or more Y groups are nitro to catalytic hydrogenation in a known manner at 0° C. to 100° C., more usually 10° C. to 50° C., conveniently at room temperature, in an aqueous acidic medium, e.g., aqueous acetic acid, employing a suitable catalyst, e.g., Raney Nickel.

On the other hand, the compounds I in which one or more Y is hydroxylamino are preferably produced by subjecting a compound I in which one or more of the Y groups are nitro to catalytic hydrogenation preferably employing a catalyst of 1 to 12% by weight of palladium on carbon. The reaction is conveniently carried out in an inert solvent of conventional type at elevated pressures and at temperatures in the range of 10° C. to 80° C., typically at about room temperature. Hydrogen pressures of from 1 to 5 atmospheres are suitably employed. The preferred solvent systems are desirably free of acid and include the lower alkanols, e.g., methanol and the chlorinated hydrocarbon, e.g., chloroform, more preferably a mixture of methanol and chloroform. Reaction time is typically 20 minutes to 3 hours.

The compounds I in which one or more Y are alkanoylamino or N-alkyl, N-alkanoylamino are preferably produced by subjecting a compound I in which one or more of the Y groups are amino or N-monoalkylamino, respectively, to reaction with the anhydride of a saturated monocarboxylic acid of 2 to 4 carbon atoms. The reaction is conveniently carried out at temperature in the range of from 0° C. to 100° C., typically at about room temperature, and in the presence of an inert solvent of conventional type, preferably a chlorinated hydrocarbon, such as chloroform.

The compounds of the formula I in which one or more Y are formamido or N-alkyl, N-formylamino may be produced by reacting a compound I in which one or more Y are amino or N-monoalkylamino, respectively, with a lower alkyl formate of 2 to 5 carbon atoms or with acetyl-formyl anhydride, preferably methyl formate, at temperatures suitably in the range of from 0° C. to 120° C., preferably 30° C. to 100° C. The reaction is conveniently carried out in an organic solvent which is preferably supplied by employing an excess of the alkyl formate or anhydride. Examples of other solvents which are inert and may be employed are dioxane and tetrahydrofuran.

The compounds I in which one or more Y are N-monoalkylamino are preferably produced by subjecting a compound I in which one or more of the Y groups is amino to reaction with a lower alkanol corresponding to the alkyl of the alkylamino group to be introduced in the presence of Raney Nickel and involves a reductive alkylation of known type. The reaction is conveniently carried out in an organic solvent at temperatures of from 30° C. to 150° C., preferably 50° C. to 100° C. Reaction time can vary fairly widely and can be typically in the range of 1 to 80 hours. While any of several conventional organic solvents may be employed, it is usually convenient to employ an excess of the lower alkanol as solvent. Examples of other suitable solvents include dioxane and ethyl acetate.

The compounds I in which one or more Y are N-methylamino may also be produced from the compounds I in which one or more Y is formamido by subjecting the latter to the action of a mild reducing agent in an inert organic solvent at temperatures conveniently in the range of from minus 10° C. to plus 100° C., more usually plus 10° C. to 50° C. The preferred reducing agent is sodiumcyanoborohydride and suitable solvents include acetonitrile.

The compounds in which one or more Y are amino may be converted by well known Sandmeyer type procedures to other compounds I including those in which one or more Y are cyano, hydroxy, chloro, bromo, alkoxy or alkylthio. For example, the compound I in which one or more Y are amino may be diazotized by subjecting to the action of sodium nitrite in dilute aqueous mineral acid solution, e.g., sulfuric acid or a hydrohalic (chloride or bromide) acid solution, at temperatures suitably in the range of from minus 20° C. to plus 30° C. to obtain an aqueous solution of the diazonium salt which may then, for example, be: a) reacted with sodium cyanide/cuprous cyanide in aqueous solution at temperatures of from 20° C. to 120° C. to obtain the compounds I in which one or more Y are cyano; or b) heated at temperatures of from 50° C. to 150° C. (the diazonium salt desirably being the sulfate salt) to obtain the compound I in which one or more Y are hydroxy.

The compounds of the formula I in which one or more Y is hydroxy may also be prepared from the corresponding alkoxy derivatives, preferably methoxy derivatives, by hydrolizing such derivatives under acidic conditions. The hydrolysis is carried out in conventional manner employing the usual conditions generally utilized for converting an aromatic alkoxy to a hydroxy group, e.g., by treatment with an aqueous solution of a hydrohalic acid, preferably hydrobromic acid, at temperatures typically of from 60° C. to 120° C.

The 1-alkyl quaternary salts of the formula Iq above described in which X is bromo or iodo are preferably produced by reacting the corresponding compound of the formula I with a compound of the formula IV:

X''—R$_q$          IV in which R$_q$ is as above defined and X'' is bromo or iodo. The reaction may be carried out in a conventional manner at temperatures in the range of from 20° C. to 100° C., preferably at the reflux temperature of the reaction mixture. The reaction may be carried out in inert organic solvents of conventional type, e.g. the lower alkanols, but is preferably carried out using an excess of the compound IV as the principal or sole solvent with other solvents, e.g., methanol, being used in minor quantities where required to dissolve the compound I in the reaction mixture. The iodide is the generally preferred anion in the compound Iq.

The compounds of the formula Iq in which X is other than the iodide may be prepared from the iodide or bromide (other than the bromide) by subjecting the iodide or bromide to well known anion exchange procedures whereby the iodide or bromide is exchanged for the desired anion. Such exchanges include typical anion exchange resin techniques carried out at temperatures of from 10° C. to 30° C. and conveniently at room temperature. The exchange may also be carried out, for example, by employing the silver salt of the anion desired to be introduced and precipitating the resulting silver iodide or bromide.

The present invention further includes the 1-alkyl-1,2-dihydro derivatives of the compounds I$_q$, viz. the compounds of the formula Ir:

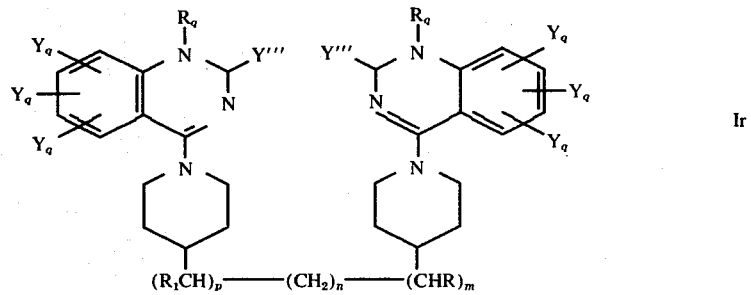

Ir wherein R$_q$, Y$_q$, m, n, p, R and R$_1$ are as above defined and Y''' is hydrogen or straight chain alkyl of 1 to 4 carbon atoms.

The compounds of the formula Ir are preferably produced from the compounds of the formula I$_q$ by reducing the latter in an inert organic solvent at temperatures of from minus 10° C. to plus 80° C., preferably plus 10° C. to 50° C. Suitable reducing agents are of conventional type for such type reductions, e.g., the alkali metal borohydrides. Inert solvents are of conventional type such as the chlorinated hydrocarbons, e.g., methylene chloride, and the lower alkanols, e.g., ethanol.

The compounds of the formula III are either known per se or may be produced from known materials by established procedures, for example, from Varma et al., J. Med. Chem. 11(1), 195 (1968) (Eng.); Thayer et al., J. Am. Chem. Soc. 70, 2330–3 (1948); British Pat. No. 1,173,244; Tolbert et al., J. Heterocycl. Chem. 1969, 6(6), 963–4 (Eng.) and U.S. Pat. Nos. 2,624,737 and 2,624,783.

Also within the scope of the compounds of the formulae I and Ir of this invention are the pharmaceutically acceptable acid addition salts thereof, e.g., the methane sulfonate, hydronitrate, maleate, fumarate and hydrochloride acid addition salts. The acid addition salts may be readily prepared from the corresponding free bases and vice versa, by conventional procedures. Compounds of the invention and their acid addition salts may also occur in hydrate form and such hydrates are treated as within the definition of the compounds and their salts as the full pharmacological equivalents thereof.

As previously indicated, the compounds of the formulae I, Iq and Ir are useful because they possess pharmacological activity in animals. In particular, the compounds I, Iq and Ir are useful as anti-obesity agents as indicated by glucose transport tests carried out on male Wistar rats which are dosed orally with 0.5–150 milligrams per kilogram of body weight of the test compound after at least 20 hours of fasting. One hour after receiving the drug each animal is sacrificed and the upper small intestine is removed and washed with glucose-saline. A 5 cm. section of the intestine is everted so that the mucosal surface is on the outside. One end of the segment is tied off and the center sac so formed is filled with oxygen saturated Kreb's biocarbonate buffer. The other end is then closed and the sac is incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Autoanalyzer procedure. Similar tests are run simultaneously with control animals. The percent inhibition of glucose transport caused by the drug is calculated from the formula:

$$I = 100 - \left(\frac{S_t - M_t}{S_c - M_c} \times 100\right)$$

where
$I$ = percent inhibition;
$S_t$ = glucose concentration (mg.%) of serosal fluid at the end of an experiment in the drug-treated animal;
$S_c$ = glucose concentration (mg.%) of serosal fluid at the end of an experiment in the control animal;
$M_t$ = glucose concentration (mg.%) of mucosal fluid at the end of an experiment in the drug-treated animal; and
$M_c$ = glucose concentration (mg.%) of mucosal fluid at the end of an experiment in the control animal.

The effective dosage of active ingredient employed for the treatment of obesity will vary depending on the particular compound employed and the severity of the condition being treated. However, in general, satisfactory results in the treatment of obesity are obtained when the compounds I, Iq and Ir are administered orally at a daily dosage of from about 0.1 milligrams to about 150 milligrams per kilogram of animal body weight, preferably given in divided doses two to four times a day, or in sustained release form. For most large animals in need of such treatment, the total daily dosage is from about 10 to 1000 milligrams. Dosage forms suitable for internal use comprise from about 3 to about 500 milligrams of the active compound in intimate admixture with a solid or liquid pharmaceutically acceptable carrier or diluent.

Certain of the compounds of this invention are represented by those of Examples 13F and 13N are also useful as anti-diabetic agents in the treatment of diabetes whether the onset was during the juvenile or mature period as indicated by the lowering of blood glucose in loading and non-loading hypoglycemic tests. In the glucose-loading test 6 to 8-week old male Royal Hart mice are fasted and then are given 10 – 200 mg./kg. of the test compound orally. One and one-half hours later, the mice are given orally 2000 mg./kg. of a glucose challenge. Twenty-five minutes later, the mice are anesthetized with 85 mg./kg. of sodium hexobarbital and 5 minutes later blood is collected via cardiac puncture. The blood samples are placed in an autoanalyzer cup containing 0.025 milliliters of heparin (1,000 units per milliliter); and the samples capped, shaken, and stored. The glucose content is determined by the autoanalyzer potassium ferric-cyanide N-2b method and are compared with a control group, which receives orally 0.5% carboxymethyl cellulose vehicle. The non-loading test is carried out in the same manner, except that anesthetsizing and blood collecting are done two hours after administrating the test compound and the glucose loading is omitted.

The anti-diabetic effective dosage in the treatment of diabetes will vary depending on the particular compound employed and the severity of the condition being treated. However, in general, satisfactory results are obtained on oral administration of a daily dosage of from about 1 to about 200 mg./kg., preferably given in divided doses two to four times per day, or in sustained release form. For most large mammals, the total daily dosage is from about 80 milligrams to about 1000 milligrams. Dosage forms suitable for internal use comprise from about 20 to about 500 milligrams of active compound in intimate admixture with a solid or liquid pharmaceutically-acceptable carrier or diluent.

For the above uses, the compounds of the formula I, Ir and Iq are preferably combined with one or more conventional pharmaceutically acceptable carriers, and such other conventional adjuvants as may be desired or necessary, and the resulting composition administered orally in such forms as tablets, capsules, granules, dispersible powders, elixers, syrups, suspensions and the like. Such compositions may be prepared according to any method known in the art for the manufacture of pharmaceutical compositions. In general, the compositions may be prepared according to any method known in the art for the manufacture of pharmaceutical compositions. In general, the compositions of the invention adapted for either oral administration may contain 1% to 90% by weight of the active ingredient in combination with the inert carrier, more usually 3% to 40%.

The preferred pharmaceutical compositions from the standpoint of preparation and ease of administration are solid compositions, particularly hard-filled capsules and tablets.

Tablets and capsules containing the ingredients indicated below may be prepared by conventional techniques and are useful in treating obesity or diabetes at a dose of one tablet or capsule 2 to 4 times a day.

| Ingredients | Weight (mg.) Tablet | Capsule |
|---|---|---|
| 1,2-Bis[4-[1-(7-chloroquinazolinyl-4)piperidyl]ethane] | 25 | 25 |
| Tragacanth | 10 | — |
| Lactose | 197.5 | 250 |
| Corn Starch | 25 | |
| Talcum | 15 | |

-continued

| Ingredients | Weight (mg.) Tablet | Capsule |
|---|---|---|
| Magnesium stearate | 2.5 | |

The following pharmaceutical composition is formulated with the indicated amount of active agent using conventional techniques. The oral liquid suspension represents a formulation useful as a unit dose and may be administered 2 to 4 times a day in the treatment of obesity.

| Ingredients | oral (mg.) liquid suspension |
|---|---|
| 1,2-Bis[4-[1-(7-chloro quinazolinyl-4)piperidyl]ethane] | 50 (or less) |
| sodium carboxy methyl cellulose U.S.P. | 12.5 |
| magnesium aluminum silicate | 47.5 |
| flavor | q.s. |
| color | q.s. |
| methyl paraben, U.S.P. | 4.5 |
| polysorbate 80 (e.g. Tween 80), U.S.P. | 5 |
| propyl parabe, U.S.P. | 1.0 |
| sorbitol solution, 70%, U.S.P. | 2500 |
| buffer agent to adjust pH for desired stability | q.s. |
| water | q.s. to 5 m |

The preferred compounds of the invention are characterized by one or more of the following features: (a) the compounds of the formula I; (b) the compounds in which p and m are 1, more preferably with n being 0 to 2; (c) the compounds in which Y' as well as Y" and Y''' are hydrogen or alkyl, more preferably hydrogen; (d) at least one Y and $Y_q$ group in each A and B ring being hydrogen; and (e) the Y and $Y_q$ groups being from the group of hydrogen, halo, alkyl, nitro, trifluoromethyl, amino and methylenedioxy, more preferably from the group of hydrogen, halo, alkyl, nitro and trifluoromethyl with at least one Y and $Y_q$ in each A and B ring being other than hydrogen.

Another group of the compounds I are those described in my above-referred to prior application Ser. No. 291,652 in which p and m are 1, Y' is hydrogen or alkyl and each Y is hydrogen, halo, alkyl, alkoxy, nitro or two adjacent Y together form 6,7-methylenedioxy or 6,7-ethylenedioxy.

Preferred compounds of the invention include bis{4-[1(7-nitroquinazolinyl-4)piperidyl]ethane} or 1,3-propane}, bis{4-[1-(6,7-dimethylquinazolinyl-4)piperidyl]ethane} or 1,3-propane} and bis{4-[1-(7-chloroquinazolinyl-4)piperidyl]ethane} or 1,3-propane}, with the more preferred compound of interest being 1,2-bis{4-[1-(7-chloroquinazolinyl-4)piperidyl]ethane}.

The following examples are given for the purpose of illustration only:

EXAMPLE 1.

1,3-Bis{4-[1-(6,7-dimethylquinazolinyl-4)piperidyl]-propane}dihydrochloride and free base form.

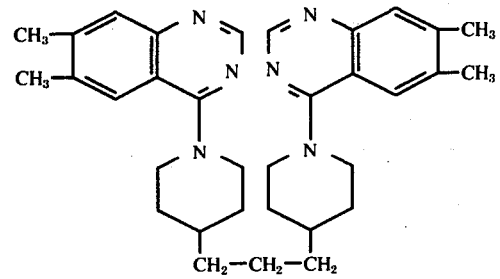

A mixture of 5.0 g. of 4-chloro-6,7-dimethylquinazoline, 2.73 g. of 1,3-bis(piperidyl-4)propane, 25 ml. of isopropanol and 3.0 g. of sodium carbonate is refluxed for 3 hours, then filtered and the filtrate evaporated in vacuo to a small volume. Trituration with anhydrous diethyl ether yields solids of the free base form of the title compound which is then dissolved in a mixture of chloroform and ethanol saturated with hydrogen chloride followed by addition of diethyl ether to obtain 1,3-bis{4-[1-(6,7-dimethylquinazolinyl-4)piperidyl]-propane}dihydrochloride, m.p. > 270° C.

The analogously prepared dimethanesulfonate acid addition salt form of the title compound of Example 1 has a melting point of 170° C.

EXAMPLE 2

1,3-Bis{4-[1-(6,7-dimethoxyquinazolinyl-4)piperidyl]-propane}dihydrochloride and free base form.

A. A mixture of 5.0 g. of 4-chloro-6,7-dimethoxyquinazoline, 2.31 g. of 1,3-bis(piperidyl-4)propane, 50.0 ml. of isopropanol and 2.5 g. of sodium carbonate is refluxed for 2 hours, then filtered and the filtrate evaporated in vacuo to obtain an oil which is triturated with 100 ml. of anhydrous ether to obtain white solids which are filtered off, washed with diethyl ether and recrystallized from ethanol/water (95:5) to obtain the title compound in free base form, m.p. 140° C. and 149°–151° C.

B. The free base form of the title compound is dissolved in a mixture of 30 ml. of chloroform and 30 ml. of ethanol and there is added thereto hydrogen chloride saturated ethanol until the solution is strongly acidic. The resulting crystals are recovered by filtering and then washed twice with ethanol to obtain the title compound in dihydrochloride acid addition salt form, m.p. 240° C. (decomp.).

EXAMPLE 3

1,3-Bis{4-[1-(2-chloro-6,7-dimethoxyquinazolinyl-4)piperidyl]propane}

In a flask fitted with a magnetic stirrer and reflux condensor and purged with nitrogen, a mixture of 2.0 g. of 2,4-dichloro-6,7-dimethoxyquinazoline, 1.92 g. of 1,3-bis(piperidyl-4)propane, 2.01 g. of sodium carbonate and 25 ml. of dioxane is refluxed under nitrogen for 4 hours. The solids are filtered off and washed with methylene chloride/chloroform. The filtrate is evaporated to yield a crude product which is triturated with ether. The residue is recrystallized from ethanol/- methylene chloride to obtain the heading compound, m.p. 210°–212° C.

The compounds of the formula II employed in the preparation of the compounds of the formula I are either known per se or may be prepared from known materials by known procedures. The 4-halo-6,7-ethylenedioxyquinazolines are preferably prepared according to the following reaction scheme:

Step 2 is a conventional aromatic nitration involving the reaction of the compound V with nitric acid in the presence of acetic acid at a temperature of from 20° C. to 100° C., more usually 40° C. to 80° C.

Step 3 is a conventional reduction of an aromatic nitro group preferably effected by hydrogenation employing a 5–10% palladium on charcoal catalyst. Glacial acetic acid is a preferred solvent for the reduction

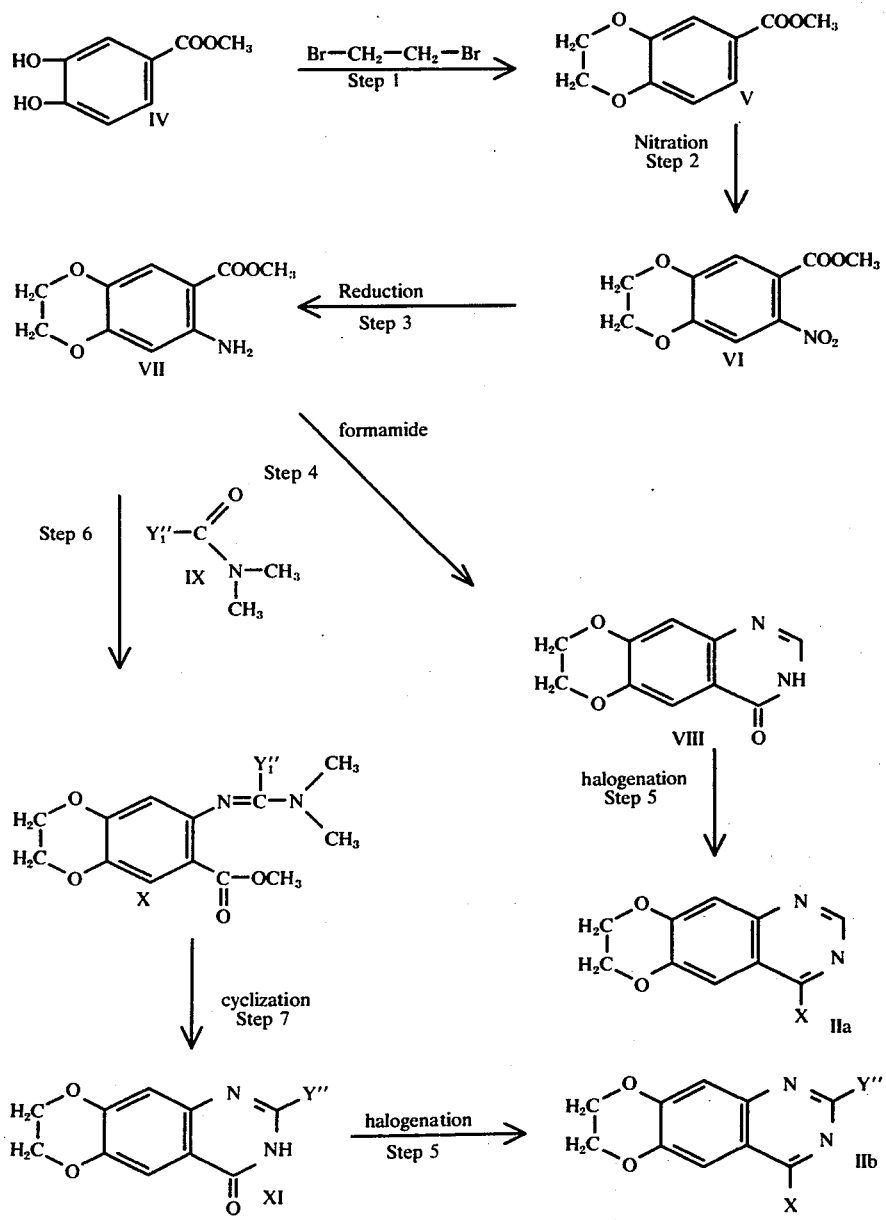

In the above reaction scheme X is as previously defined and Y'''$_1$ is alkyl of 1 to 4 carbon atoms.

The reaction of Step 1 involves reacting the compound of the formula IV with 1,2-dibromoethane in the presence of a strong base which is preferably an alkali metal alkoxide, more preferably sodium methoxide. An excess of the 1,2-dibromoethane is usually employed and may be used as the solvent for the reaction. However, an inert conventional solvent such as an alcohol, e.g. methanol, is preferably employed. The reaction may be carried out at temperatures of from 20° C. to 120° C., preferably 40° C. to 80° C.

which may be carried out at temperatures of from 0° C. to 60° C., preferably 10° C. to 40° C.

Step 4 involves cyclizing the compound VII with formamide which may be employed in excess as the solvent. The reaction may be carried out at temperatures of from 100° C. to 220° C., preferably 150° C. to 215° C., more preferably under reflux conditions.

Step 5 is a conventional halogenation of cyclic keto group preferably carried out employing a phosphorus oxyhalide as the halogenating agent. The phosphorus oxyhalide is preferably employed in excess as the solvent for the reaction which is conveniently effected at the reflux temperature of the system. The reaction may be carried out under an inert atmosphere, e.g., nitrogen, but such conditions are not necessary.

Step 6 involving the reaction of compound VII with a compound of the formula IX is conveniently carried out in an inert atmosphere at temperatures of from 10° C. to 100° C., preferably 30° C. to 60° C., and in the presence of a phosphorus oxyhalide, preferably phosphorus oxychloride. Alternately and preferably, the compound IX is first reacted with the phosphorus oxyhalide at 10° C. to 100° C. and the resulting reaction product then reacted with the compound VII.

Step 7 involves the cyclization of a compound X employing ammonia in the presence of ammonium chloride. The reaction is conveniently conducted at temperatures of from 50° C. to 150° C. in a sealed bomb employing excess ammonia as the liquid reaction medium.

In the reaction of Steps 1–7, inclusive, the desired reaction product may be recovered by working up by conventional procedures.

EXAMPLE 4

4-Chloro-6,7-ethylenedioxyquinazoline

Step A: Preparation of 3,4-ethylenedixoybenzoic acid methyl ester.

A solution of 4.20 g. of 3,4-dihydroxybenzoic acid methyl ester in 10.0 ml. of methanol is combined with 7.0 g. of sodium methoxide and then 15.0 g. of 1,2-dibromoethane is added. The resulting mixture is refluxed under nitrogen for 24 hours, then cooled, filtered, evaporated in vacuo and the resulting oil dissolved in 50 ml. of chloroform. The resulting solution after again filtering is chromatographed over 100 ml. of silica gel eluting with chloroform to obtain 3,4-ethylenedioxybenzoic acid methyl ester, m.p. 43°–45° C.

Step B: Preparation of 6-nitro-3,4-ethylenedioxybenzoic acid methyl ester.

To a solution of 5.0 g. of 3,4-ethylenedioxybenzoic acid methyl ester in 5.0 mls. of glacial acetic acid is added dropwise 5.0 mls. of 70% nitric acid at 50°–60° C. After addition the reaction mixture is kept at 55° C. for one hour, then cooled and 50 mls. of ice water added. The resulting precipitate is recovered by filtering, water washed and dried to obtain 6-nitro-3,4-ethylenedioxybenzoic acid methyl ester, m.p. 115°–118° C.

Step C: Preparation of 6-amino-3,4-ethylenedioxybenzoic acid methyl ester.

A mixture of 6.0 g. of 6-nitro-3,4-ethylenedioxybenzoic acid methyl ester, 150 mg. of 5% palladium on charcoal and 20 mls. of glacial acetic acid is hydrogenated under an initial hydrogen pressure of 30–40 p.s.i. and without external heating. After four hours the reaction mixture is filtered diluted with 80 ml. of ice water, stirred up one half hour and the resulting precipitate filtered off, water washed and dried to obtain 6-amino-3,4-ethylenedioxybenzoic acid methyl ester, m.p. 73°–77° C.

Step D: Preparation of 6,7-ethylenedioxyquinazolin-4(3H)-one.

A mixture of 2.0 g. of 6-amino-3,4-ethylenedioxybenzoic acid methyl ester and 6 ml. of 99% formamide is refluxed for 1.5 hours, then cooled, diluted with 5 ml. of water and the resulting precipitate filtered off, water washed and dried to obtain 6,7-ethylenedioxyquinazolin-4(3H)-one, m.p. 275° C.

Step E: Preparation of 4-chloro-6,7-ethylenedioxyquinazoline.

A mixture of 25.3 g. of 6,7-ethylenedioxyquinazolin-4(3H)-one and 50 ml. of phosphorus oxychloride is refluxed for 10 minutes, cooled, and added with stirring to one liter of ice. After addition of concentrated ammonia the resulting mixture is extracted with chloroform and the chloroform solution chromatographed through 300 mls. of silica gel while eluting with chloroform. Evaporation of the eluent yields 4-chloro-6,7-ethylenedioxyquinazoline, m.p. 169°–174° C.

EXAMPLE 5

2-Methyl-4-chloro-6,7-ethylenedioxyquinazoline

Step A: Preparation of 2-(α-dimethylaminoethylideneamino)-4,5-ethylenedioxybenzoic acid methyl ester.

To a mixture prepared by mixing 15.2 g. of N,N-dimethylacetamide and 40 ml. of phosphorus oxychloride is added portionwise 35.0 g. of 6-amino-3,4-ethylenedioxyzenzoic acid methyl ester while maintaining 40°–45° C. The reaction mixture is stirred for 4 hours at 40°–60° C. the reaction mixture is added to ice, treated with concentrated ammonia, extracted with chloroform and the chloroform solution evaporated to obtain an oil of 2-(α-dimethylaminoethylideneamino)-4,5-ethylenedioxybenzoic acid methyl ester.

Step B: Preparation of 2-methyl-6,7-ethylenedioxyquinazolin-4(3H)-one.

A mixture of 12 g. 2-(α-dimethylaminoethylideneamido)-4,5-ethylenedioxybenzoic acid methyl ester, 12 g. of ammonia chloride and 100 ml. of liquid ammonia is contained in a sealed bomb and heated at 110° C. for 10 hours. The ammonia is evaporated off and the resulting solids washed several times with water and dried to yield 2-methyl-6,7-ethylenedioxyquinazolin-4(3H)-one, m.p. 275° C.

Step C: Preparation of 2-methyl-4-chloro-6,7-ethylenedioxyquinazoline.

Following essentially the procedure of Step E of Example 4 there is obtained 2-methyl-4-chloro-6,7-ethylenedioxyquinazoline, m.p. 168.5°–169.5° C.

EXAMPLE 6

1,3-bis{4-[1-(7-aminoquinazolinyl-4)piperidyl]-propane}dimethanesulfonate

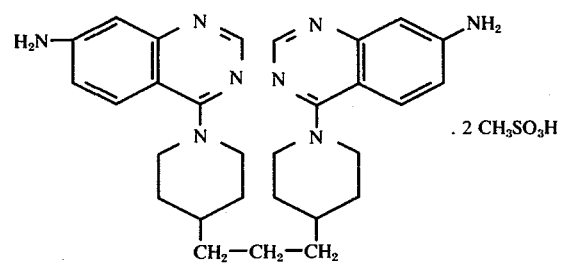

A mixture of 1.0 g. of 1,3-bis{4-[1-(7-nitroquinazolinyl-4)piperidyl]propane}dihydrochloride, 1.0 g. of Raney Nickel and 50 ml. of a 20% aqueous acetic acid at 25° C. is hydrogenated under an initial 50 psi hydrogen pressure for 1½ hours. The resulting mixture is filtered to remove the catalyst and, after washing with methanol, the filtrate is evaporated to an oil which is triturated with cold dilute ammonia solution to obtain crystals which are dried and taken up in 50 ml. of chloroform followed by the addition of 1 ml. of ammonia. After filtration the filtrate is filtered through 30 ml. of silica gel using a methanol/chloroform (5:95) as eluent. The resulting solution is evaporated to an oil and triturated with ether to obtain crystals (m.p. 120°–123° C.) which are treated with methanesulfonic acid in methanol/chloroform (50:50) followed by evaporation and crystallization from ether to obtain 1,3-bis{4-[1-(7-aminoquinazolinyl-4)piperidyl]propane}dimethanesulfonate, m.p. > 285° C.

EXAMPLE 7

1,3-bis{4-[1-(7-acetamidoquinazolinyl-4)piperidyl]propane}

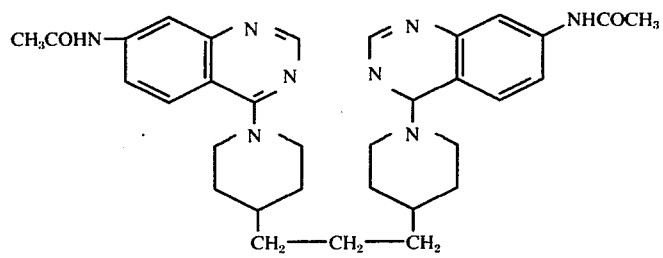

To a solution of 1.55 q. of 1,3-bis{4-[1-(7-aminoquinazolinyl-4)piperidyl]propane} in 20 ml. of dry chloroform is added 0.95 ml. of acetic anhydride at room temperature. After one half hour the reaction mixture is filtered and the crude product recovered. The filtrate is evaporated to dryness and the residue is triturated with aqueous ammonia and the resulting solids dried and extracted with hot chloroform. The chloroform extract is cooled, filtered and the resulting solids combined with the crude product previously obtained and recrystallized from chloroform containing a very small amount of methanol to obtain 1,3-bis{4-[1-(7-acetamidoquinazolinyl-4)piperidyl]propane}, m.p. 273°–276° C.

EXAMPLE 8

1,3-bis{4-[1-(7-hydroxylaminoquinazolinyl-4)piperidyl]propane} dihydrochloride.

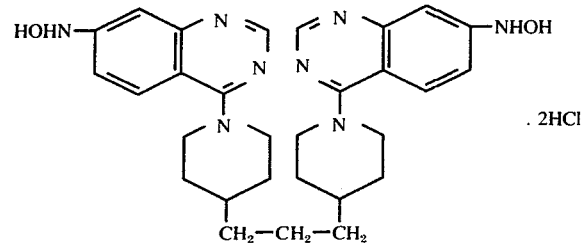

A mixture of 4.0 g. of 1,3-bis{4-[1-(7-nitroquinazolinyl-4)piperidyl]propane}dihydrochloride, 500 mg. of 5% palladium on carbon, 100 ml. of methanol and 100 ml. of chloroform is hydrogenated under an initial hydrogen pressure of 40 psi for 1 hour. The resulting mixture is filtered to remove catalyst and, after washing with methanol, the filtrate is evaporated to a small volume yielding crystals which are recovered by filtering, washed with methanol and dried to obtain 1,3-bis{4-[1-(7-hydroxylaminoquinazolinyl-4)piperidyl]propane} dihydrochloride, m.p. 220° C. (decomp.).

EXAMPLE 9

1,3-bis{4-[1-(1-methyl-7-chloroquinazolinyl-4)piperidyl]propane} diodide

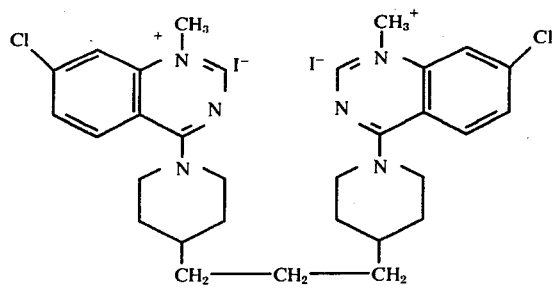

A mixture of 5.0 g. of 1,3-bis{4-[1-(7-chloroquinazolinyl-4)piperidyl]propane}, 25 ml. of methyl iodide and 2.0 ml. of methanol is heated at reflux under nitrogen for one hour. The resulting mixture is evaporated to remove excess methyl iodide, diluted with ether and the resulting crystalline material recovered by filtering and dried to obtain 1,3-Bis{4-[1-(1-methyl-7-chloroquinazolinyl-4)piperidyl]propane} diodide, m.p. 190° C. (decomp.).

EXAMPLE 10

1,3-bis{4-[1-(6-dimethylaminoquinazolinyl-4)piperidyl]propane} dimethanesulfonate.

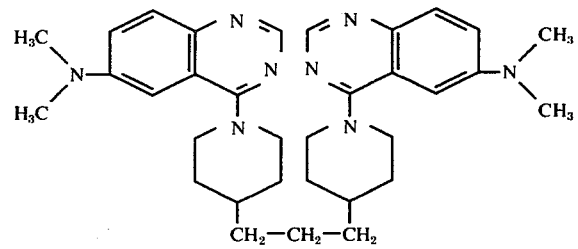

Step A: Preparation of 2-nitro-5-dimethyl aminobenzoic acid.

To a solution of 30 g. of 2-dimethylaminobenzoic acid in 100 ml. of glacial acetic acid is added dropwise 15 ml. of 70% nitro acid while maintaining a temperature of 40°–60° C. The resulting mixture is allowed to cool to room temperature and treated slowly with ice water to a volume of 600 ml. The resulting crystals are recovered by filtering, washed several times with water and are partially dried by sucking air through the filter. The crystals are then washed with chloroform and dried to obtain 2-nitro-5-dimethylaminobenzoic acid, m.p. 185°–187° C.

STEP B: Preparation of 2-amino-5-dimethylaminobenzoic acid.

A mixture of 18 g. of 2-nitro-5-dimethylaminobenzoic acid, 1.0 liter of a 50:50 mixture of dimethylacetamide/methanol and 18 g. of Raney Nickel is hydrogenated at a hydrogen pressure of 40–50 psi for 2 hours. The resulting mixture is filtered, washed with methanol and the total filtrate evaporated to a solid which is broken up, washed with ether and dried to obtain 2-amino-5-dimethylaminobenzoic acid, m.p. 231°–234° C. (decomp.).

STEP C: Preparation of 6-dimethylaminoquinazolin-4(3H)-one.

A mixture of 14.6 g. of 2-amino-5-dimethylaminobenzoic acid and 75 ml. of formamide is refluxed for 40 minutes, cooled to room temperature, 100 ml. of water added, the crystals broken up and recovered by filtering. After washing several times with water, the solids are dried to obtain 6-dimethylaminoquinazolin-4(3H)one, m.p. 233°–236° C.

STEP D: Preparation of 6-dimethylamino-4-chloroquinazoline.

A mixture of 12.4 g. of 6-dimethylamino-quinazolin-4(3H)-one and 50 ml. of phosphorus oxychloride is refluxed under nitrogen for 10 minutes, cooled to room temperature, 150 ml. of ether added, the crystals recovered by filtering, washed with ether and dried. The solids are added to 500 ml. of ice-water, concentrated ammonia is added to neutralize the solution which is extracted with 1.0 liter of chloroform. The chloroform extract is dried and filtered through 300 ml. of silica gel using chloroform as an eluant. Evaporation of the eluant yields 6-dimethylamino-4-chloroquinazoline, m.p. 126°–127.5° C.

STEP E: Preparation of 1,3-bis{4-[1-(6-dimethylaminoquinazolinyl-4)piperidyl]propane}dimethanesulfonate.

A mixture of 1.83 g. of 6-dimethylamino-4-chloroquinazoline, 925 mg. of 1,3-bis(piperidyl-4)propane, 1.6 g. of sodium carbonate and 20 ml. of isopropanol is refluxed for one hour. The resulting mixture is filtered and the filtrate evaporated to an oil which is treated with ether to obtain the titled product in free base form, m.p. 137°–138° C. This product is dissolved in absolute ethanol containing methanesulfonic acid and ether is added to obtain 1,3-bis{4-[1-(6-dimethylaminoquinazolinyl-4) piperidyl]propane}dimethanesulfonate, m.p. 265.5°–267.5° C.

EXAMPLE 11

Following the procedure of Step E of Example 10, there is obtained 1,2-bis{4-[1-(6-dimethylaminoquinazolinyl-4) piperidyl]ethane}, m.p. 215°–217° C.

EXAMPLE 12

1,3-bis{4-[1-(7-ethylaminoquinazolinyl-4)piperidyl]propane}dihydrochloride.

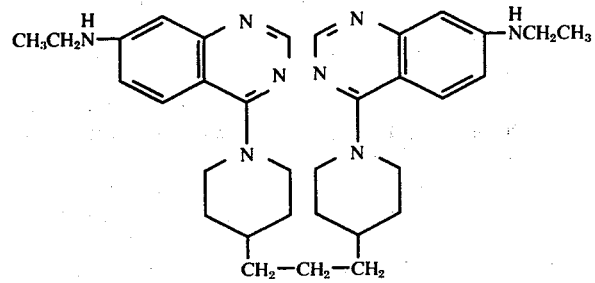

A mixture of 1.0 g. of 1,3-bis{4-[1-(7-aminoquinazolinyl-4)piperidyl]propane}, 18 g. of Raney Nickel and 70 mls. of ethanol is refluxed under nitrogen for 60 hours. The resulting mixture is filtered and the filtered catalyst washed with hot ethanol. The resulting filtrate is concentrated to a small volume and ethanolic hydrogen chloride added until the resulting solution is acidic. Ether is added and the resulting crystalline material is recovered by filtering to obtain 1,3-bis{4-[1-(7-ethylaminoquinazolinyl-4)piperidyl]propane}dihydrochloride, m.p. 233°–238° C. (decomp.).

EXAMPLE 13

Following the general procedure of Examples 1–3, the following compounds of the invention are prepared.

A. 1,3-bis{4-[1-(6,7-dimethoxy-2-methylquinazolinyl-4) piperidyl]propane}, m.p. 148°–149° C,
B. 1,3-bis{4-[1-(6-methoxyquinazolinyl-4)piperidyl]propane}, dihydrochloride form, m.p. 249° C (decomp.),
C. 1,3-bis{4-[1-(6-chloroquinazolinyl-4)piperidyl]propane}, m.p. 162°–163° C, dihydrochloride form, m.p. 246° C (decomp.),
D. 1,3-bis{4-[1-(quinazolinyl-4)piperidyl]propane}, m.p. 128°–129° C, dihydrochloride form, m.p. >270° C,
E. 1,3-bis{4-[1-(5-methoxyquinazolinyl-4)piperidyl]propane}, m.p. 223°–225° C,
F. 1,3-bis{4-[1-(7-nitroquinazolinyl-4)piperidyl]propane}, dimethanesulfonate form, m.p. 90°–95° C (decomp.),
G. bis{4-[1-(6,7-dimethylquinazolinyl-4)piperidyl]methane}, m.p. dimethanesulphonate form 285°–286° C,
H. bis{4-[1-(7-nitroquinazolinyl-4)piperidyl]methane}, m.p. 212°–213.5° C,
I. bis{4-[1-(6,7,8-trimethoxyquinazolinyl-4)piperidyl]methane}, m.p. dihydrate dimethanesulphonate form, 206°–207° C,
J. 1,3-bis{4-[1-(6,7,8-trimethoxyquinazolinyl-4) piperidyl]propane}dihydrochloride, m.p. 115° C. (decomp.).
K. bis{4-[1-(6,7-dimethoxyquinazolinyl-)piperidyl]methane}, m.p. dimethanesulphonate form 283°–284° C, L. bis{4-[1-(6-methoxyquinazolinyl-4)piperidyl]methane}, m.p. dimethanesulphonate form 269°–271° C, M. bis{4-[1-(6-chloroquinazolinyl-4)piperidyl)methane}, m.p. dihydrochloride form 266°–269° C (decomp.), N. bis{4-[1-(7-chloroquinazolinyl-4)piperidyl]methane}, m.p. dimethanesulphonate form 284°–286° C, O. 1,2-bis{4-[1-(7-nitroquinazolinyl-4)piperidyl]ethane}, m.p. 218°–220° C, P. 1,2-bis{4-[1-(6,7-dimethylquinazolinyl-4)piperidyl]ethane}, m.p. dimethanesulphonate form 247° C (decomp.), Q. 1,3-bis{4-[1-(7-chloroquinazolinyl-4)piperidyl]propane}, m.p. hydrate dihydrochloride form 110° C (decomp.), R. 1,3-bis{4-[1-(6,7-dichloroquinazolinyl-4)piperidyl]propane}, m.p. 204°–205° C, S. 1,2-bis{4-[1-(7-trifluoromethylquinazolinyl-4)piperidyl]ethane}, m.p. dimethanesulphonate form 245°–247° C, T. 1,3-bis{4-[1-(7-trifluoromethylquinazolinyl-4)piperidyl]propane}, m.p. dimethanesulphonate form 181°–185° C, U. 1,3-bis{4-[1-(6-nitroquinazolinyl-4)piperidyl]propane}, m.p. dihydrochloride form 262°–265° C (decomp.), V. 1,3-bis{4-[1-(2-methyl-6,7,8-trimethoxyquinazolinyl-4) piperidyl]propane}, m.p. 147° C, W. 1,3-bis{4-[1-(6,7-methylenedioxyquinazolinyl-4)piperidyl]propane}, m.p. dimethanesulphonate form 272° C (decomp.), X. 1,3-bis{4-[1-(6-methylquinazolinyl-4)piperidyl]propane}, m.p. 130.5° C.

Y. 1,3-bis{4-[1-(7,8-dimethylquinazolinyl-4)piperidyl]propane}, m.p. dihydrochloride form 280°–285° C (decomp.), Z. 1,3-bis{4-[1-(7-methylquinazolinyl-4)piperidyl]propane}, m.p. dimethanesulphonate form 215°–220° C (decomp.), AA. 1,3-bis{4-[1-(6,8-dichloroquinazolinyl-4)piperidyl]propane}, m.p. dihydrochloride form 230°–240° C, AB. 1,3-bis{4-[1-(7-methoxyquinazolinyl-4)piperidyl]propane}, m.p. dimethanesulphonate form 165° C, AC. 1,2-bis{4-[1-(6-methoxyquinazolinyl-4)piperidyl]ethane}, m.p. dihydrochloride form 272° C, AD. 1,2-bis{4-[1-(7-methylquinazolinyl-4)piperidyl]ethane},m.p. dimethanesulphonate form 238°–243° C, AE. 1,2-bis{4-[1-(7-chloroquinazolinyl-4)piperidyl]ethane}, m.p. 213° C, AF. 1,2-bis{4-[1-(7-methoxyquinazolinyl-4)piperidyl]ethane}, m.p. dimethanesulphonate form 272°–273° C, AG. 1,2-bis{4-[1-(6-chloroquinazolinyl-4)piperidyl]ethane}, m.p. 229° C, AH. 1,2-bis{4-[1-(6,7-dimethoxyquinazolinyl-4)piperidyl]ethane}, m.p. 247° C (decomp.), AI. 1,2-bis{4-[1-(7,8-dimethylquinazolinyl-4)piperidyl]ethane}, m.p. dimethanesulphonate form 232°–234° C, AJ. 1,2-bis{4-[1-(6-nitroquinazolinyl-4)piperidyl]ethane}, m.p. 226°–228° C, and AK. 1,3-bis{4-[6-methylthioquinazolinyl-4)piperidyl]propane}.

AL. 1,3-bis{4-[1-(6,7-ethylenedioxyquinazolinyl-)piperidyl]propane}dihydrochloride, m.p. 238°–240° C.

AM. 1,3-bis{4-[1-(2-methyl-6,7-ethylenedioxyquinazolinyl-4)piperidyl]propane}dihydrochloride, m.p. 270° C. (decomp.).

EXAMPLE 14

Following the procedure of Example 9, the following additional compounds of the invention are prepared:

A. 1,3-bis{4-[1-(1,6,7-trimethylquinazolinyl-4) piperidyl]propane}diiodide, m.p. 303° C. (decomp.).

EXAMPLE 15

Following the general procedure of Examples 1–3, the following compounds of the invention are prepared:

A. bi-4-[1-(7-chloroquinazolinyl-4)piperidyl]dimethanesulfonate, m.p. above 270° C.

B. bi-4-[1-(6,7-dimethylquinazolinyl-4)piperidyl]-dimethanesulfonate, m.p. above 270° C.

EXAMPLE 16

Additional compounds of the invention are:

A. 1,2-bis{4-[1-(7-chloroquinazolinyl-4)-1'-(6,7-dimethylquinazolinyl-4)piperidyl]ethane} m.p. 168°–170.5° C. and a melting point of 224°–228° C. in dimethanesulfonate salt form.

B. 1,3-bis{4-[1-(6-cyanoquinazolinyl-4)piperidyl]propane}dimethanesulfonate.

C. 1,3-bis{4-[1-(7-formamidoquinazolinyl-4) piperidyl]propane}.

D. 1,3-bis{4-[1-(7-methylaminoquinazolinyl-4) piperidyl]propane}dihydrochloride.

EXAMPLE 17

The compound of the foregoing Example 13F may be prepared in other acid addition salt forms in accordance with the standard procedures referred to herein, for example: (a) the dihydrochloride, m.p. 245°–247° C.; (b) the dihydronitrate, m.p. 168°–170° C.; (c) the dihydrosulfate, m.p. 175°–180° C.; (d) the dimaleate, m.p. 184°–185° C.; (e) the p-toluenesulfonate monohydrate form, m.p. 250°–252° C.; and (f) the malonate, m.p. 164°–165° C.

EXAMPLE 18

1,3-Bis{4-[1-(1,6,7-trimethyl-1,2-dihydroquinazolinyl-4) piperidyl]propane}

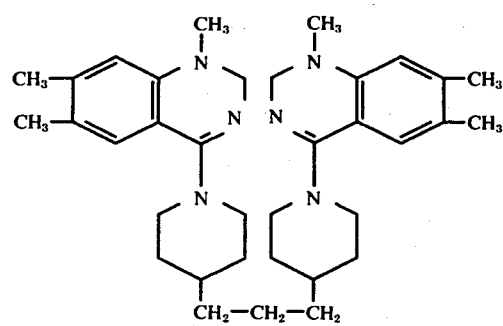

To a mixture of 50 ml. of methylene chloride and 100 ml. of ethanol is added 9.46 g. of 1,3-bis{4-[1-(1,6,7-trimethylquinazolinyl-4)piperidyl]propane}diiodide and to this suspension is added while stirring a total of 1.334 g. of sodium borohydride in two portions. The suspended material goes into solution amidst considerable bubbling and ice is added as required to maintain the temperature below 25° C. After 10 minutes from the first addition of the borohydride 15 mls. of acetic acid is added while maintaining stirring and the resulting solution is stripped to a thin oil which is washed with methylene chloride, then twice with 2 N. sodium hydroxide solution and then with water. The resulting liquid is evaporated to yield a crystalline material which is washed with pentane/ether to obtain 1,3-bis{4-[1-(1,6,7-trimethyl-1,2-dihydroquinazolinyl-4)piperidyl]propane}, m.p. 155° C. (decomp.).

EXAMPLE 19

Following the procedure of Example 18, the following additional compounds of the formula Ir are prepared:

A.     1,3-bis{4-[1-(1-methyl-7-chloro-1,2-dihydroquinazolinyl-4)piperidyl]propane}.

B.     1,3-bis{4-[1-(1-methyl-7-nitro-1,2-dihydroquinazolinyl-4)piperidyl]propane}.

What is claimed is:

1. A compound selected from the group consisting of:

a. compounds of the formula I:

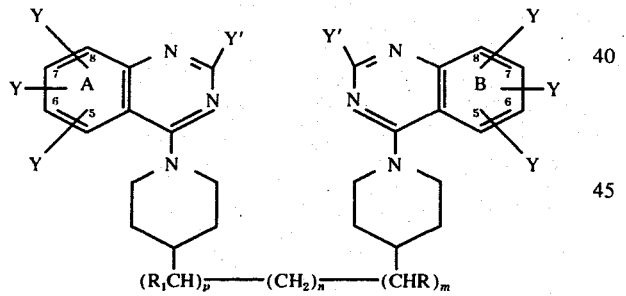

I b. compounds of the formula Iq:

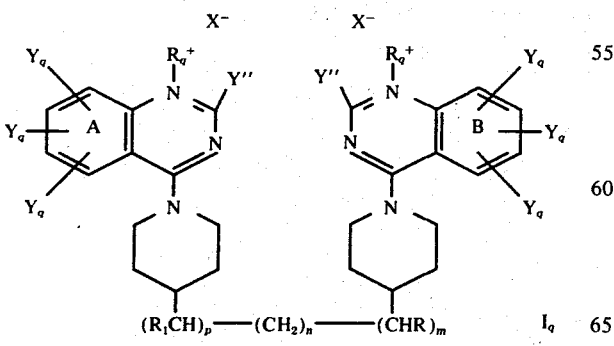

Iq and c. compounds of the formula Ir:

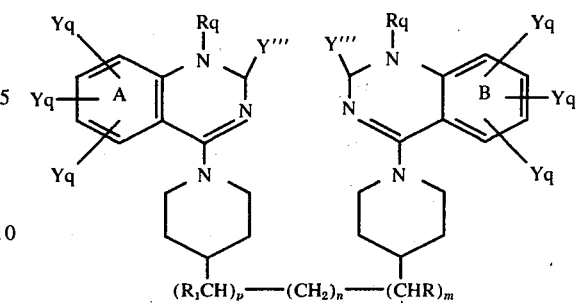

Ir wherein

R and $R_1$ are independently hydrogen or alkyl of 1 to 4 carbon atoms, $n$ is 0 to 4, $m$ is 0 to 1, $p$ is 0 or 1, each Y is independently hydrogen, fluoro, chloro, bromo, alkyl of 1 to 4 carbon atoms, alkoxy of 1 to 3 carbon atoms, alkylthio of 1 to 3 carbon atoms, hydroxy, formamido, trifluoromethyl, nitro, cyano, amino, hydroxylamino, N-monoalkylamino of 1 to 4 carbon atoms, N,N-dialkylamino in which each alkyl is of 1 to 3 carbon atoms, alkanoylamino of 2 to 4 carbon atoms, N-alkyl (of 1 to 3 carbon atoms), N-alkanoyl (of 2 to 4 carbon atoms) amino or N-alkyl (of 1 to 3 carbon atoms), N-formylamino or two adjacent Y together form 6,7-methylenedioxy or 6,7-ethylenedioxy (with the other Y on each A and B ring so substituted being hydrogen), subject to the proviso that: (1) adjacent Ys are not both tert-butyl; (2) no more than 2 Ys in each A and B ring are substituents selected from the group consisting of trifluoromethyl, nitro, cyano, hydroxy, formamido, alkylthio, amino, N-alkylamino, N,N-dialkylamino, hydroxylamino, alkanoylamino, N-alkyl, N-alkanoylamino and N-alkyl, N-formylamino; (3) when any Y in an A or B ring is amino, cyano, hydroxylamino, N-alkylamino, N,N-dialkylamino, alkanoylamino, formamido, N-alkyl, N-alkanoylamino or N-alkyl, N-formylamino, then any dissimilar Y is selected from the group consisting of hydrogen, fluoro, chloro, bromo, alkyl and alkoxy; and (4) when any Y is hydroxy, then no other Y is a dissimilar substituent selected from the group consisting of alkoxy and alkylthio, each Y' is independently hydrogen, chloro, bromo or alkyl of 1 to 4 carbon atoms, each Y'' is independently hydrogen, chloro, bromo or straight chain alkyl of 1 to 4 carbon atoms, each Y''' is independently hydrogen or straight chain alkyl of 1 to 4 carbon atoms, each $Y_q$ is independently hydrogen, fluoro, chloro, bromo, alkyl of 1 to 4 carbon atoms, alkoxy of 1 to 3 carbon atoms, trifluoromethyl or nitro or two adjacent Yq together form 6,7-methylenedioxy or 6,7-ethylenedioxy with the other Y on each A and B ring so substituted being hydrogen, subject to the provisos that: (1) adjacent Yq's are not both tert-butyl; and (2) no more than two Yq's in each A and B ring are substituents selected from the group consisting of trifluoromethyl and nitro, Rq is alkyl of 1 to 4 carbon atoms which is unbranched on the α-carbon atom, and X is a pharmaceutically acceptable inorganic anion, or a pharmaceutically acceptable acid addition salt of a compound of the formula I and Ir.

2. A compound of claim 1 having the formula:

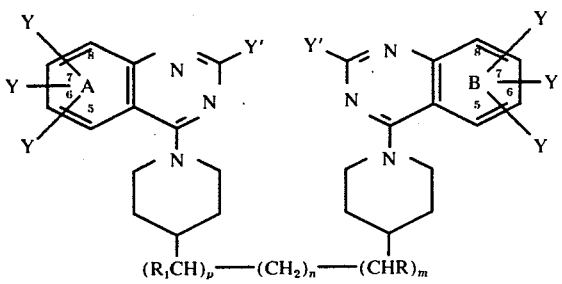

wherein
R and $R_1$ are independently hydrogen or alkyl of 1 to 4 carbon atoms,
$n$ is 0 to 4,
$m$ is 0 to 1,
$p$ is 0 or 1,
each Y is independently hydrogen, fluoro, chloro, bromo, alkyl of 1 to 4 carbon atoms, alkoxy of 1 to 3 carbon atoms, alkylthio of 1 to 3 carbon atoms, hydroxy, formamido, trifluoromethyl, nitro, cyano, amino, hydroxylamino, N-monoalkylamino of 1 to 4 carbon atoms, N,N-dialkylamino in which each alkyl is of 1 to 3 carbon atoms, alkanoylamino of 2 to 4 carbon atoms, N-alkyl (of 1 to 3 carbon atoms), N-alkanoyl (of 2 to 4 carbon atoms) amino or N-alkyl (of 1 to 3 carbon atoms), N-formylamino or two adjacent Y together form 6,7-methylenedioxy or 6,7-ethylenedioxy (with the other Y on each A and B ring so substituted being hydrogen), subject to the proviso that: (1) adjacent Ys are not both tert-butyl; (2) no more than 2 Ys in each A and B ring are substituents selected from the group consisting of trifluoromethyl, nitro, cyano, hydroxy, formamido, alkylthio, amino, N-alkylamino, N,N-dialkylamino, hydroxylamino, alkanoylamino, N-alkyl, N-alkanoylamino and N-alkyl, N-formylamino; (3) when any Y in an A or B ring is amino, cyano, hydroxylamino, N-alkylamino, N,N-dialkylamino, alkanoylamino, formamido, N-alkyl, N-alkanoylamino or N-alkyl, N-formylamino, then any dissimilar Y is selected from the group consisting of hydrogen, fluoro, chloro, bromo, alkyl and alkoxy; and (4) when any Y is hydroxy, then no other Y is a dissimilar substituent selected from the group consisting of alkoxy and alkylthio, and each Y' is independently hydrogen, chloro, bromo or alkyl of 1 to 4 carbon atoms, or a pharmaceutically acceptable acid addition salt thereof.

3. A compound of claim 1 having the formula

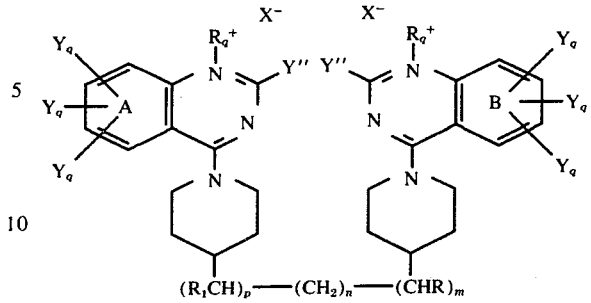

wherein
R and $R_1$ are independently hydrogen or alkyl of 1 to 4 carbon atoms,
each Yq is independently, hydrogen, fluoro, chloro, bromo, alkyl of 1 to 4 carbon atoms, alkoxy of 1 to 3 carbon atoms, trifluoromethyl or nitro or two adjacent Yq together form 6,7-methylenedioxy or 6,7-ethylenedioxy with the other Y on each A and B ring so substituted being hydrogen, subject to the provisos that: (1) adjacent Yq's are not both tert-butyl; and (2) no more than two Yq's in each A and B ring are substituents selected from the group consisting of trifluoromethyl and nitro,
Rq is alkyl of 1 to 4 carbon atoms which is unbranched on the α-carbon atom, and
X is a pharmaceutically acceptable inorganic anion,
Y'' is hydrogen, chloro, bromo or straight chain alkyl of 1 to 4 carbon atoms,
$n$ is 0 to 4,
$p$ is 0 or 1, and
$m$ is 0 or 1.

4. A compound of claim 1 of the formula:

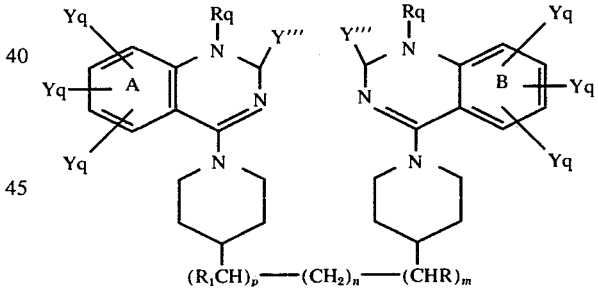

Ir wherein
R and $R_1$ are independently hydrogen or alkyl of 1 to 4 carbon atoms,
each Yq is independently, hydrogen, fluoro, chloro, bromo, alkyl of 1 to 4 carbon atoms, alkoxy of 1 to 3 carbon atoms, trifluoromethyl or nitro or two adjacent Yq together form 6,7-methylenedioxy or 6,7-ethylenedioxy with the other Y on each A and B ring so substituted being hydrogen, subject to the provisos that: (1) adjacent Yq's are not both tert-butyl; and (2) no more than two Yq's in each A and B ring are substituents selected from the group consisting of trifluoromethyl and nitro,
Rq is alkyl of 1 to 4 carbon atoms which is unbranched on the α-carbon atom,
each Y''' is independently hydrogen or straight chain alkyl of 1 to 4 carbon atoms, $n$ is 0 to 4,
$p$ is 0 or 1, and
$m$ is 0 or 1,
or a pharmaceutically acceptable acid addition salt thereof.

5. A compound of claim 2 in which $m$ and $p$ are 1, Y' is hydrogen or alkyl and each Y is independently hydrogen, fluoro, chloro, bromo, alkyl or alkoxy or two adjacent Y together form 6,7-methylenedioxy or 6,7-ethylenedioxy.

6. A compound of claim 2 in which $p$ and $m$ are 1.

7. A compound of claim 6 in which R and $R_1$ are hydrogen.

8. A compound of claim 7 in which Y' is hydrogen or alkyl.

9. A compound of claim 8 in which at least one Y in each of the A and B rings is hydrogen.

10. A compound of claim 9 in which the Ys are selected from the group consisting of hydrogen, fluoro, chloro, bromo, alkyl, nitro, trifluoromethyl, amino and methylenedioxy.

11. A compound of claim 10 in which the Ys are selected from the group consisting of hydrogen, fluoro, chloro, bromo, alkyl, nitro and trifluoromethyl with at least one Y in each A and B ring being other than hydrogen.

12. A compound of claim 8 in which $n$ is 0 to 2.

13. A compound of claim 10 in which $n$ is 0 to 2.

14. A compound of claim 2 in acid addition salt form.

15. The compound of claim 2 which is 1,3-bis{4-[1-(7-nitroquinazolinyl-4)piperidyl]propane}.

16. The compound of claim 15 in acid addition salt form.

17. The compound of claim 15 in dimethanesulfonate acid addition salt form.

18. The compound of claim 2 which is 1,3-bis{4-[1-(6,7-dimethylquinazolinyl-4)piperidyl]propane}.

19. The compound of claim 2 which is 1,3-bis{4-[1-(7-chloroquinazolinyl-4)piperidyl]propane}.

20. The compound of claim 2 which is 1,2-bis{4-[1-(6,7-dimethylquinazolinyl-4)piperidyl]ethane}.

21. The compound of claim 2 which is 1,3-bis{4-[1-(7-trifluoromethylquinazolinyl-4)piperidyl]propane}.

22. The compound of claim 2 which is 1,3-bis{4-[1-(6,7-methylenedioxyquinazolinyl-4)piperidyl]propane}.

23. The compound of claim 2 which is 1,2-bis{4-[1-(7-methylquinazolinyl-4)piperidyl]ethane}.

24. The compound of claim 2 which is 1,2-bis{4-[1-(6-chloroquinazolinyl-4)piperidyl]ethane}.

25. The compound of claim 2 which is 1,2-bis{4-[1-(6-nitroquinazolinyl-4)piperidyl]ethane}.

26. A compound of claim 3 in which $p$ and $m$ are 1.

27. A compound of claim 26 in which R and $R_1$ are hydrogen.

28. A compound of claim 27 in which Y'' is hydrogen.

29. A compound of claim 28 in which at least one $Y_q$ in each of the A and B rings is hydrogen.

30. A compound of claim 29 in which the $Y_q$ is selected from the group consisting of hydrogen, fluoro, chloro, bromo, alkyl, nitro, trifluoromethyl and methylenedioxy.

31. A compound of claim 30 in which the $Y_q$ is selected from the group consisting of hydrogen, fluoro, chloro, bromo, alkyl, nitro and trifluoromethyl with at least one $Y_q$ in each A and B ring being other than hydrogen.

32. A compound of claim 28 in which $n$ is 0 to 2.

33. A compound of claim 30 in which $n$ is 0 to 2.

34. The compound of claim 3 which is 1,3-bis{4-[1-(1-methyl-7-chloroquinazolinyl-4)piperidyl]propane}diiodide.

35. The compound of claim 3 which is 1,3-bis{4-[1-(1,6,7-trimethylquinazolinyl-4)piperidyl]propane}diiodide.

36. A compound of claim 4 in which $p$ and $m$ are 1.

37. A compound of claim 36 in which R and $R_1$ are hydrogen.

38. A compound of claim 37 in which Y''' is hydrogen.

39. A compound of claim 38 in which at least one $Y_q$ in each of the A and B rings is hydrogen.

40. A compound of claim 39 in which the $Y_q$ is selected from the group consisting of hydrogen, fluoro, chloro, bromo, alkyl, nitro, trifluoromethyl and methylenedioxy.

41. A compound of claim 40 in which the $Y_q$ is selected from the group consisting of hydrogen, fluoro, chloro, bromo, alkyl, nitro and trifluoromethyl with at least one $Y_q$ in each A and B ring being other than hydrogen.

42. A compound of claim 38 in which $n$ is 0 to 2.

43. A compound of claim 40 in which $n$ is 0 to 2.

44. A compound of claim 4 in acid addition salt form.

45. The compound of claim 4 which is 1,3-bis{4-[1-(1,6,7-trimethyl-1,2-dihydroquinazolinyl-4)piperidyl]propane}.

46. The compound of claim 4 which is 1,3-bis{4-[1-(1-methyl-7-chloro-1,2-dihydroquinazolinyl-4)piperidyl]propane}.

47. The compound of claim 4 which is 1,3-bis{4-[1-(1-methyl-7-nitro-1,2-dihydroquinazolinyl-4)piperidyl]propane}

48. The compound of claim 2 which is 1,2-bis{4-[1-(7,8-dimethylquinazolinyl-4)piperidyl]ethane}.

49. The compound of claim 2 which is 1,2-bis{4-[1-(7-chloroquinazolinyl-4)piperidyl]ethane}.

50. The compound of claim 2 which is 1,2-bis{4-[1-(6,7-dimethylquinazolinyl-4)piperidyl]ethane}.

51. A pharmaceutical composition comprising an inert pharmaceutically acceptable carrier and 3 to 500 milligrams of a compound of claim 1.

52. The method of treating obesity in animals comprising administering orally to an animal an anti-obesity effective amount of a compound of claim 1.

* * * * *